(12) United States Patent
Ortiz

(10) Patent No.: US 8,211,142 B2
(45) Date of Patent: Jul. 3, 2012

(54) METHOD FOR HYBRID GASTRO-JEJUNOSTOMY

(76) Inventor: Mark S. Ortiz, Milford, OH (US)

( * ) Notice: Subject to any disclaimer, the term of this patent is extended or adjusted under 35 U.S.C. 154(b) by 1449 days.

(21) Appl. No.: 11/277,289

(22) Filed: Mar. 23, 2006

(65) Prior Publication Data

US 2006/0217748 A1  Sep. 28, 2006

Related U.S. Application Data

(63) Continuation-in-part of application No. 10/675,705, filed on Sep. 30, 2003, now abandoned, and a continuation-in-part of application No. 10/675,077, filed on Sep. 30, 2003, now Pat. No. 7,452,363.

(51) Int. Cl.
*A61B 17/08* (2006.01)
(52) U.S. Cl. .................................... 606/213; 606/151
(58) Field of Classification Search .............. 606/139, 606/153, 151, 157, 198, 213, 215, 216, 232; 60/201, 207; 600/201, 207
See application file for complete search history.

(56) References Cited

U.S. PATENT DOCUMENTS

| | | |
|---|---|---|
| 2,004,013 A | 6/1935 | Reed |
| 2,004,014 A | 6/1935 | Sanford |
| 2,004,172 A | 6/1935 | Niday |
| 4,841,888 A | 6/1989 | Mills et al. |
| 5,041,129 A | 8/1991 | Hayhurst et al. |
| 5,080,663 A | 1/1992 | Mills et al. |
| 5,217,486 A | 6/1993 | Rice et al. |
| 5,269,809 A | 12/1993 | Hayhurst et al. |
| 5,376,101 A | 12/1994 | Green et al. |
| 5,398,670 A | 3/1995 | Ortiz et al. |
| 5,437,681 A | 8/1995 | Meade et al. |
| 5,462,558 A | 10/1995 | Kolesa et al. |
| 5,464,415 A | 11/1995 | Chen et al. |
| 5,503,635 A | 4/1996 | Sauer et al. |
| 5,514,159 A | 5/1996 | Matula et al. |
| 5,531,678 A * | 7/1996 | Tomba et al. ................. 606/142 |
| 5,540,705 A | 7/1996 | Meade et al. |

(Continued)

FOREIGN PATENT DOCUMENTS

RU  2208400  7/2003

(Continued)

OTHER PUBLICATIONS

USPTO Non-Final Rejection for U.S. Appl. No. 10/675,705, dated May 4, 2007. cited by other.

(Continued)

*Primary Examiner* — Corrine M McDermott
*Assistant Examiner* — Melissa Ryckman

(57) ABSTRACT

Disclosed herein are methods for joining one piece to tissue to another piece of tissue. In one embodiment, the method can include inserting an applier device having an actuation portion into a first body lumen through a natural body orifice, forming a first opening in a first piece of tissue within the first lumen and a second opening in a second piece of tissue defining a portion of a second lumen adjacent to the first piece of tissue, and inserting the applier device through the first and second openings such that the actuation portion is between the first and second piece of tissue. The method can further include deploying a fastener into the first and second pieces of tissue through the actuation portion of the applier device, thereby joining the first and second pieces of tissue to form an anastomosis between the first and second lumens.

16 Claims, 8 Drawing Sheets

U.S. PATENT DOCUMENTS

| | | | |
|---|---|---|---|
| 5,571,119 A | 11/1996 | Atala | |
| 5,584,861 A | 12/1996 | Swain et al. | |
| 5,649,938 A | 7/1997 | Allen et al. | |
| 5,676,670 A | 10/1997 | Kim | |
| 5,709,693 A | 1/1998 | Taylor | |
| 5,713,910 A | 2/1998 | Gordon et al. | |
| 5,755,730 A | 5/1998 | Swain et al. | |
| 5,797,920 A | 8/1998 | Kim | |
| 5,814,071 A | 9/1998 | McDevitt et al. | |
| 5,843,088 A | 12/1998 | Barra et al. | |
| 5,853,422 A * | 12/1998 | Huebsch et al. | 606/213 |
| 5,860,992 A | 1/1999 | Daniel et al. | |
| 5,868,760 A | 2/1999 | McGuckin, Jr. | |
| 5,887,594 A | 3/1999 | LoCicero, III | |
| 5,899,921 A | 5/1999 | Caspari et al. | |
| 5,902,321 A | 5/1999 | Caspari et al. | |
| 5,954,731 A | 9/1999 | Yoon | |
| 6,007,544 A | 12/1999 | Kim | |
| 6,010,515 A | 1/2000 | Swain et al. | |
| 6,036,694 A | 3/2000 | Goble et al. | |
| 6,200,329 B1 | 3/2001 | Fung et al. | |
| 6,312,446 B1 | 11/2001 | Huebsch et al. | |
| 6,346,111 B1 | 2/2002 | Gordon et al. | |
| 6,358,259 B1 | 3/2002 | Swain et al. | |
| 6,379,368 B1 | 4/2002 | Corcoran et al. | |
| 6,443,962 B1 | 9/2002 | Gaber | |
| 6,454,778 B2 | 9/2002 | Kortenbach | |
| 6,461,320 B1 | 10/2002 | Yencho et al. | |
| 6,494,888 B1 | 12/2002 | Laufer et al. | |
| 6,500,195 B2 | 12/2002 | Bonutti | |
| 6,506,196 B1 | 1/2003 | Laufer | |
| 6,524,328 B2 | 2/2003 | Levinson | |
| 6,540,789 B1 | 4/2003 | Silverman et al. | |
| 6,543,456 B1 * | 4/2003 | Freeman | 128/898 |
| 6,558,400 B2 | 5/2003 | Deem et al. | |
| 6,572,629 B2 | 6/2003 | Kalloo et al. | |
| 6,632,227 B2 | 10/2003 | Adams | |
| 6,663,639 B1 | 12/2003 | Laufer et al. | |
| 6,699,263 B2 * | 3/2004 | Cope | 606/153 |
| 6,709,441 B2 | 3/2004 | Bolduc et al. | |
| 6,712,836 B1 | 3/2004 | Berg et al. | |
| 6,719,763 B2 | 4/2004 | Chung et al. | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,773,441 B1 | 8/2004 | Laufer et al. | |
| 6,821,858 B2 | 11/2004 | Namatame et al. | |
| 6,835,200 B2 | 12/2004 | Laufer et al. | |
| 6,869,395 B2 | 3/2005 | Page et al. | |
| 6,908,427 B2 | 6/2005 | Fleener et al. | |
| 6,949,116 B2 | 9/2005 | Solymar et al. | |
| 6,955,643 B2 | 10/2005 | Gellman et al. | |
| 7,004,949 B2 | 2/2006 | Yencho et al. | |
| 2001/0023352 A1 | 9/2001 | Gordon et al. | |
| 2002/0107530 A1 | 8/2002 | Sauer et al. | |
| 2002/0193809 A1 | 12/2002 | Meade et al. | |
| 2003/0032967 A1 | 2/2003 | Park et al. | |
| 2003/0083674 A1 | 5/2003 | Gibbens | |
| 2003/0109900 A1 | 6/2003 | Martinek | |
| 2003/0120265 A1 | 6/2003 | Deem et al. | |
| 2003/0120292 A1 * | 6/2003 | Park et al. | 606/153 |
| 2003/0171760 A1 | 9/2003 | Gambale | |
| 2003/0181924 A1 | 9/2003 | Yamamoto et al. | |
| 2003/0191481 A1 | 10/2003 | Nguyen et al. | |
| 2003/0225312 A1 | 12/2003 | Suzuki et al. | |
| 2003/0229296 A1 | 12/2003 | Ishikawa et al. | |
| 2003/0233104 A1 | 12/2003 | Gellman et al. | |
| 2003/0233108 A1 | 12/2003 | Gellman et al. | |
| 2004/0002720 A1 | 1/2004 | Kortenbach et al. | |
| 2004/0006351 A1 | 1/2004 | Gannoe et al. | |
| 2004/0024386 A1 | 2/2004 | Deem et al. | |
| 2004/0034369 A1 | 2/2004 | Sauer et al. | |
| 2004/0059350 A1 | 3/2004 | Gordon et al. | |
| 2004/0082963 A1 | 4/2004 | Gannoe et al. | |
| 2004/0098050 A1 | 5/2004 | Foerster et al. | |
| 2004/0122452 A1 | 6/2004 | Deem et al. | |
| 2004/0122453 A1 | 6/2004 | Deem et al. | |
| 2004/0122473 A1 | 6/2004 | Ewers et al. | |
| 2004/0147958 A1 | 7/2004 | Lam et al. | |
| 2004/0162568 A1 | 8/2004 | Saadat et al. | |
| 2004/0193184 A1 | 9/2004 | Laufer et al. | |
| 2004/0194790 A1 | 10/2004 | Laufer et al. | |
| 2004/0210243 A1 | 10/2004 | Gannoe et al. | |
| 2004/0215058 A1 | 10/2004 | Zirps et al. | |
| 2005/0015101 A1 | 1/2005 | Gibbens et al. | |
| 2005/0033319 A1 | 2/2005 | Gambale et al. | |
| 2005/0055038 A1 | 3/2005 | Kelleher et al. | |
| 2005/0070921 A1 | 3/2005 | Ortiz et al. | |
| 2005/0070926 A1 | 3/2005 | Ortiz | |
| 2005/0070931 A1 | 3/2005 | Li et al. | |
| 2005/0070934 A1 | 3/2005 | Tanaka et al. | |
| 2005/0070935 A1 | 3/2005 | Ortiz | |
| 2005/0070939 A1 | 3/2005 | Beaupre | |
| 2005/0075653 A1 | 4/2005 | Saadat et al. | |
| 2005/0075654 A1 | 4/2005 | Kelleher | |
| 2005/0143760 A1 | 6/2005 | Imran | |
| 2005/0143762 A1 | 6/2005 | Paraschac et al. | |
| 2005/0149067 A1 | 7/2005 | Takemoto et al. | |
| 2005/0165419 A1 | 7/2005 | Sauer et al. | |
| 2005/0192599 A1 | 9/2005 | Demarais | |
| 2005/0192601 A1 | 9/2005 | Demarais | |
| 2005/0203488 A1 | 9/2005 | Michlitsch et al. | |
| 2006/0217748 A1 | 9/2006 | Ortiz | |

FOREIGN PATENT DOCUMENTS

| | | |
|---|---|---|
| WO | 9519140 A1 | 7/1995 |
| WO | WO-95/19140 | 7/1995 |
| WO | 9917662 | 4/1999 |
| WO | 0061013 | 10/2000 |
| WO | WO-00/61012 | 10/2000 |
| WO | 0110312 A1 | 2/2001 |
| WO | WO-01/10312 | 2/2001 |
| WO | 0166001 A2 | 9/2001 |
| WO | WO-01/66001 | 9/2001 |
| WO | 0189393 A1 | 11/2001 |
| WO | WO-01/89393 | 11/2001 |
| WO | 02096327 A2 | 12/2002 |
| WO | WO-02/096327 | 12/2002 |
| WO | 03000142 A2 | 1/2003 |
| WO | 2004021894 | 3/2004 |
| WO | WO-2004/021894 | 3/2004 |
| WO | 2005034729 | 4/2005 |
| WO | WO-2005/034729 | 4/2005 |

OTHER PUBLICATIONS

USPTO Final Rejection for U.S. Appl. No. 10/675,705, dated Jan. 24, 2007. cited by other.

USPTO Non-Final Rejection for U.S. Appl. No. 10/675,705, dated Aug. 7, 2006. cited by other.

USPTO Non-Final Rejection for U.S. Appl. No. 10/675,705, dated Feb. 27, 2006. cited by other.

USPTO Office Action for U.S. Appl. No. 10/675,705, dated Jan. 10, 2006. cited by other.

EPO Search Report for Application No. 04256046.6, dated Feb. 9, 2005. cited by other.

EPO Communication for Application No. 04256046.6, dated Dec. 27, 2005. cited by other.

EPO Communication dor Application No. 04256046.6, dated Oct. 17, 2006. cited by other.

EPO Search Report for Application No. 04256018.5, dated Dec. 22, 2004. cited by other.

* cited by examiner

METHOD FOR HYBRID GASTRO-JEJUNOSTOMY

CROSS-REFERENCE TO RELATED APPLICATIONS

The present application is a continuation-in-part of U.S. application Ser. No. 10/675,705, filed Sep. 30, 2003, and entitled "Single Lumen Access Deployable Ring for Intralumenal Anastomosis," now abandoned, and also a continuation-in part of U.S. application Ser. No. 10/675,077, filed Sep. 30, 2003, and entitled "Applier for Fastener for Single Lumen Access Anastomosis," now U.S. Pat. No. 7,452,363 both of which are incorporated by reference herein.

FIELD OF THE INVENTION

The present invention relates to methods for joining one piece of tissue to another piece of tissue.

BACKGROUND OF THE INVENTION

The percentage of the world population suffering from morbid obesity is steadily increasing. Severely obese persons are susceptible to increased risk of heart disease, stroke, diabetes, pulmonary disease, and accidents. Because of the effect of morbid obesity on the life of the patient, methods of treating morbid obesity are being researched.

Numerous non-operative therapies for morbid obesity have been tried with virtually no permanent success. Dietary counseling, behavioral modification, wiring a patient's jaws shut, and pharmacological methods have all been tried, and though temporarily effective, have failed to correct the condition. Further, techniques such as introducing an object in the stomach to fill the stomach, such as an esophago-gastric balloon, have also been used to treat the condition. However, such approaches tend to cause irritation to the stomach and are not effective long-term.

Surgical treatments for morbid obesity have been increasingly used with greater success. These approaches may be generalized as those that reduce the effective size of the stomach, limiting the amount of food intake, and those that create malabsorption of the food that is eaten. For instance, some patients benefit from adjustable gastric bands (AGB) that are advantageously laparoscopically placed about the stomach to form a stoma of a desired size that allows food to fill an upper portion of the stomach, causing a feeling of satiety. To allow adjustment of the size of the stoma after implantation, a fluid conduit communicates between an inwardly presented fluid bladder of the AGB to a fluid injection port subcutaneously placed in front of the patient's sternum. A syringe needle may then inject or withdraw fluid as desired to adjust the AGB.

Although an effective approach to obesity for some, other patients may find the lifestyle changes undesirable, necessitated by the restricted amount of food intake. In addition, the medical condition of the patient may suggest the need for a more permanent solution. To that end, surgical approaches have been used to alter portions of the stomach and/or small intestine available for digesting food. Creating an anastomosis, or the surgical formation of a passage between two normally distinct vessels, is a critical step in many of these surgical procedures. This is particularly true of gastric bypass procedures in which two portions of the small intestine are joined together and another portion of the small intestine is joined to the stomach of the patient. This is also true of surgery to alleviate a blockage(s) in the common bile duct by draining bile from the duct to the small intestine during surgery for pancreatic cancer. With particular reference to gastric bypass procedures, current methods of performing a laparoscopic anastomosis for a gastric bypass include stapling, suturing, and using biofragmentable rings, each of which has significant challenges.

Consequently, there is a general need for an improved method for joining one piece of tissue to another piece of tissue, and in particular for forming an anastomosis between the small bowel and the stomach.

SUMMARY OF THE INVENTION

The present invention provides methods for joining one piece of tissue to another piece of tissue. In one aspect, a method for joining tissue includes inserting an applier device having an actuation portion into a first body lumen through a natural body orifice, forming a first opening in a first piece of tissue within the first lumen and a second opening in a second piece of tissue defining a portion of a second lumen adjacent to the first piece of tissue, and inserting the applier device through the first and second openings such that the actuation portion is between the first and second pieces of tissue. The method can further include deploying a fastener into the first and second pieces of tissue through the actuation portion of the applier device to join the first and second pieces of tissue to form an anastomosis between the first and second lumens. The applier device can be inserted endoscopically into the natural body orifice, and in one embodiment where the first piece of tissue can be part of a stomach and the second piece of tissue can be part of a jejunum, the device can endoscopically access the stomach through the esophagus.

The first and second openings can be formed using a variety of techniques. In one embodiment, the distal end of the applier device can be used as a marker to facilitate formation of the first opening. The first and second openings can then be formed via a laparoscopic surgical procedure, or alternatively the first opening can be formed using a cutting member associated with a distal end of the applier device and the second opening can be formed using a cutting element that accesses a site of the second opening by a laparoscopic port. Once formed, and in order to facilitate insertion of the applier device therein, the first and second openings can be expanded using a tapered distal end of the applier device or at least one grasping element.

The techniques used to position the actuation portion between the first and second pieces of tissue and to deploy a fastener therein can vary depending upon the configuration of the applier device, and in particular, the configuration of the actuation portion of the applier device and the fastener. In one embodiment, the actuation portion of the applier device can include at least one fastener having proximal and distal ring members joined by a connecting element, with the proximal and distal ring members each having a plurality of arms extending therefrom that are adapted to engage tissue. In this embodiment, positioning the actuation portion can include positioning the distal ring member of the fastener such that it is adjacent to the second piece of tissue and positioning the proximal ring member of the fastener such that it is adjacent to the first piece of tissue. This allows the connecting element to extend between the first and second pieces of tissue. The fastener can be deployed by actuating the actuation portion such that the plurality of arms of the proximal and distal ring members move from a first resting position to a second actuated position such that the plurality of arms engage and hold together the first and second pieces of tissue. The plurality of arms of the proximal and distal ring members can be independently or simultaneously actuated to engage the first and second pieces of tissue. In one embodiment, the fastener can also optionally be disengaged from a catch located on the actuation portion that holds the fastener on the actuation portion prior to any deployment into tissue.

In another aspect, a method for forming an anastomosis can include endoscopically inserting an applier device through a natural body orifice, through a lumen and through a first opening formed in a first piece of tissue and a second opening formed in a second piece of tissue, and positioning an actuation portion of the applier device between the first and second pieces of tissue. The method can also include deploying a fastener into the first and second pieces of tissue through the actuation portion of the device to form an anastomosis therebetween.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
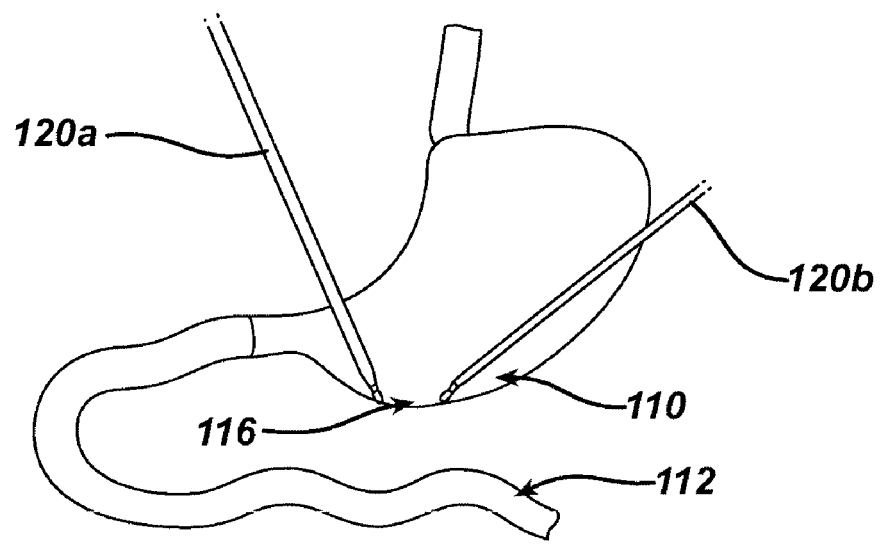
FIG. 1A is a schematic illustrating the formation of a first opening in a stomach.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods for joining one piece of tissue to another piece of tissue. In one embodiment, the method can include inserting an applier device having an actuation portion into a first body lumen through a natural body orifice, forming a first opening in a first piece of tissue within the first lumen and a second opening in a second piece of tissue defining a portion of a second lumen adjacent to the first piece of tissue, and inserting the applier device through the first and second openings such that the actuation portion is in between the first and second piece of tissue. The method can further include deploying a fastener into the first and second pieces of tissue through the actuation portion of the applier device, thereby joining the first and second pieces of tissue to form an anastomosis between the first and second lumens. One skilled in the art will appreciate that the applier device can be inserted through a variety of lumens, such as natural body lumens, and the lumens can be accessed through natural body orifices, such as the esophagus and the rectum, or through a surgically-created portal, during a variety of medical procedures which require tissues to be joined. By way of non-limiting example, such medical procedures include a Roux-en-Y procedure or other bariatric procedures which can require the joining of the jejunum to a stomach or stomach part, or bypass procedures for bypassing a cancerous or non-cancerous obstruction(s) in tissue, such as the duodenum. This method is particularly advantageous in that it minimizes the number of access lumens formed in a patient by relying on natural orifices and/or a single created lumen or portal, such as a laparoscopic portal, for the insertion of the applier device.

FIGS. 1A-1E illustrate one exemplary embodiment of a method for forming an anastomosis 114 between a part of a jejunum 112 and a part of a stomach 110. Following preparation of the patient and the surgical site as known in the art, an applier device 126 can be inserted transorally, and guided through the esophagus into the stomach 110. The applier device 126 can then be positioned at a site adjacent a wall of the stomach 110, and the tip of the applier device 126 can optionally form a slight protrusion (not shown) on the distal wall thereof. This protrusion can serve as a marker that allows a surgeon to identify the location of the applier device 126 within the stomach 110, such that the surgeon can form a first opening 116 in the stomach 110 from which the applier device 126 can exit the stomach 110. Alternatively, and in other embodiments, traditional monitoring and/or tracking techniques, such as radioopaque bands located on the distal tip of the applier device, can be used to facilitate locating and/or tracking of the applier device and formation of the first opening.

The first opening 116 can be formed using a variety of techniques, and in one embodiment, the first opening can be formed from within the stomach 110 using a cutting member (not shown), such as a blade, that is located on the distal end of the applier device 126. Alternatively, and referring to FIG. 1A, the first opening 116 can be formed using at least one cutting element (cutting elements 120a, 120b are shown), such as scissors, that can be inserted by a laparoscopic surgical technique to a location adjacent to the position of the applier device 126 external to the stomach 110. The first opening 116 can also be formed using a combination of above-mentioned laparoscopic and endoscopic techniques. Following formation, the first opening 116 can be expanded to allow the applier device 126, and in particular the actuation portion thereof, to be inserted therethrough and directed towards the jejunum 112. Any technique known in the art can be used to expand the tissue of the stomach 110, and exemplary techniques can include the use of a tapered element located on the distal end of the applier device, the use of graspers, or some other element that is adapted to hold open at least a portion of the first opening to enlarge it, and combinations thereof. This insertion technique is particularly advantageous in that it does not require the formation of a new incision to allow the applier device 126 to access the jejunum 112. As a result, the laparoscopic port used to form the first opening 116 can be left in position for the formation of a second opening 124 in the jejunum 112, as will be discussed in more detail below.

Figure 1B:
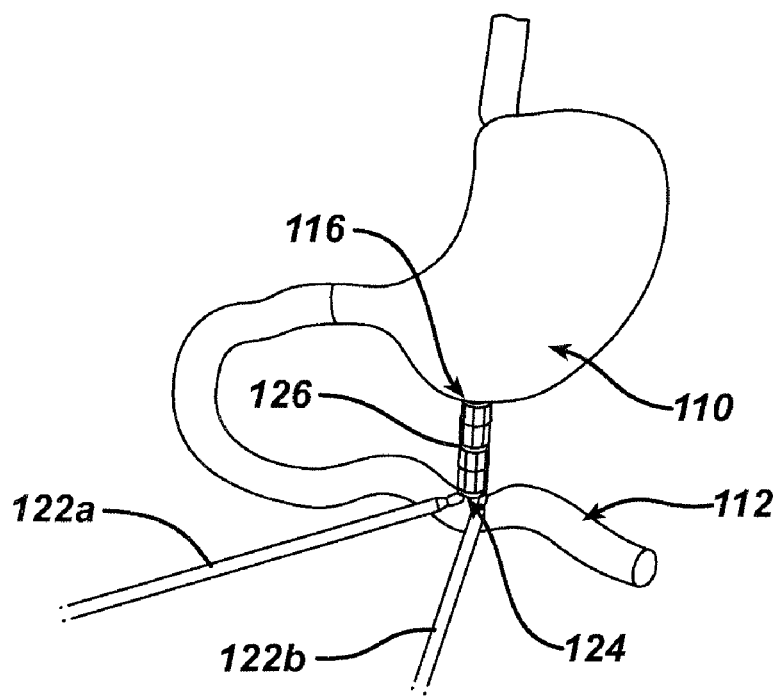
FIG. 1B is a schematic illustrating the insertion of an actuation portion of an applier device through the first opening of FIG. 1A and a second opening formed in a jejunum.

As noted above and once the applier device 126 is moved through the first opening 116 such that it is positioned at the jejunum 112, a second opening 124 for receiving the applier device 126 can be formed in the jejunum 112. The second opening 124 can be formed using techniques similar to those noted above with respect to the formation of the first opening 116 (e.g., a cutting member on the distal end of the applier device, using a cutting element(s) that accesses the site through a laparoscopic port, or combinations thereof). However in an exemplary embodiment, the second opening 124 can be formed using a cutting element(s) that accesses the site through the same laparoscopic port that was used to form the first opening 116. Following formation of the second opening 124, the applier device 126 can be inserted into and through the second opening 124 such that at least a portion of the actuation portion is positioned between the stomach 110 and the jejunum 112 to facilitate the placement of a fastener within the tissues 110, 112. As described above with respect to the formation of the first opening 116 and as shown in FIG. 1B, the second opening 124 can be expanded to facilitate insertion of the applier device 126 therein using a distal end (not shown) of the applier device 126, and additionally or alternatively, two graspers 122a, 122b that are positioned on opposed sides of the second opening 124.

Once the applier device 126 is positioned at the desired location between the stomach 110 and the jejunum 112, the actuation portion can be actuated to effect the deployment of a fastener into the tissues 110, 112. A variety of techniques can be used to actuate the actuation portion of the applier device 126 to deploy the fastener, and those techniques can depend upon the types of applier devices and fasteners used. However, in one embodiment, as will be described in more detail below, the actuation portion of the applier device can include at least one fastener having proximal and distal ring members joined by a connecting element, with the proximal and distal ring members each having a plurality of arms extending therefrom that are adapted to engage tissue. The actuation portion can also optionally include a catch for holding the fastener thereto prior to deployment into tissue.

Figure 1C:
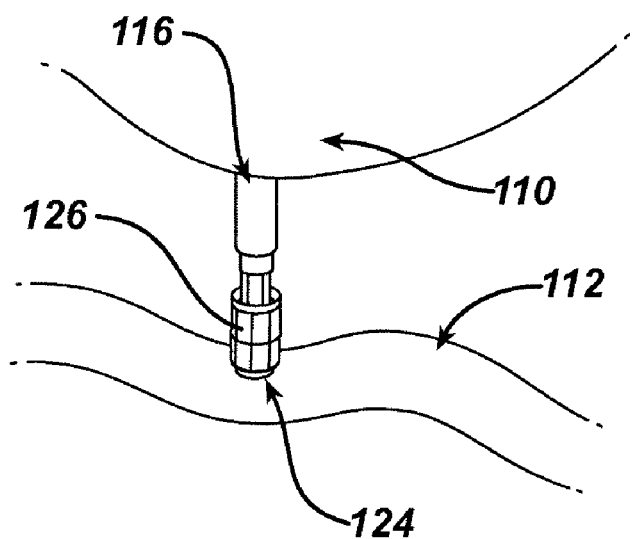
FIG. 1C is a schematic illustrating the deployment of a fastener into a distal portion of the jejunum.
Figure 1D:
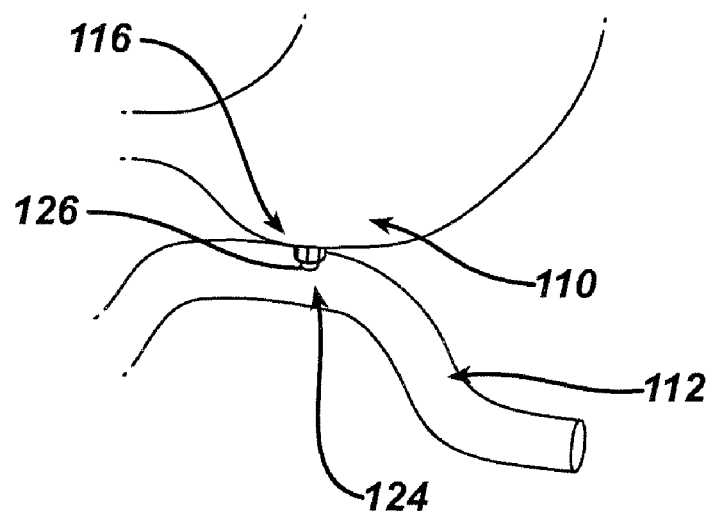
FIG. 1D is a schematic illustrating the retraction of the applier device from the jejunum.
Figure 1E:
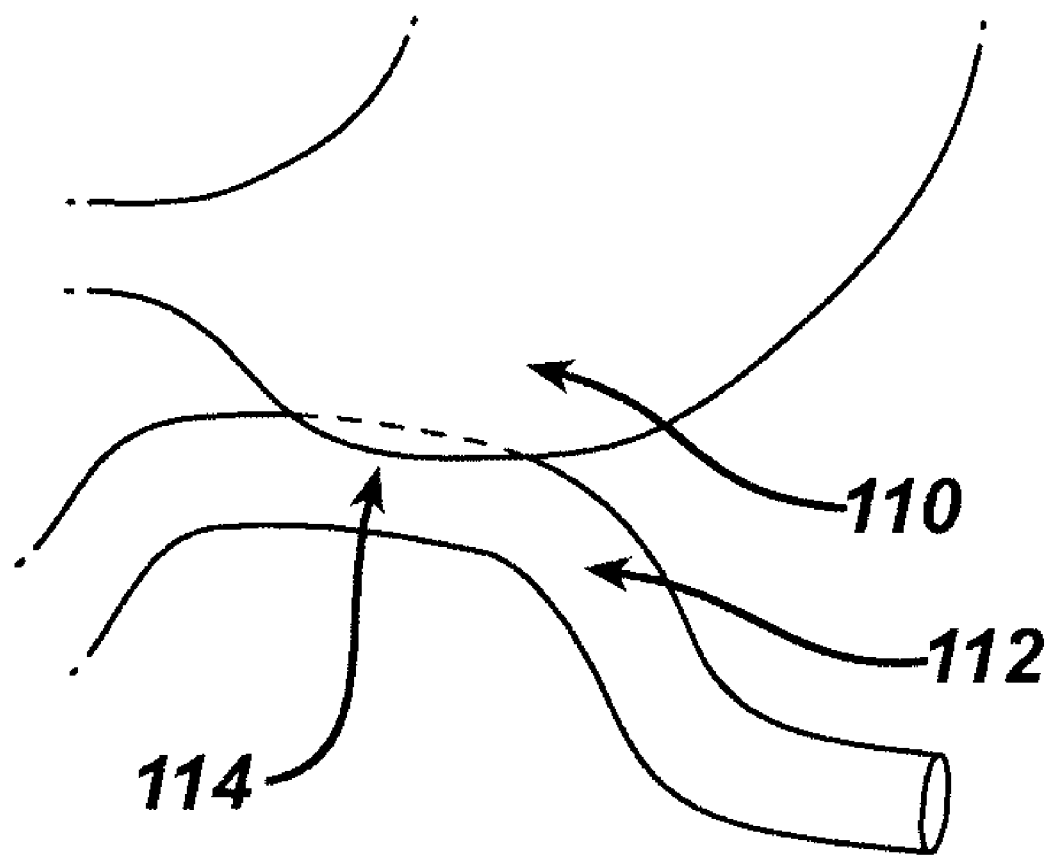
FIG. 1E is a schematic illustrating an anastomosis formed between the stomach and the jejunum as a result of the method FIGS. 1A-1D.

When such an applier device is used, actuation can cause the fastener to optionally be released from the catch and the plurality of arms formed on the proximal and distal ring members (not shown) to move from a first resting position to a second actuated position such that they engage and hold together opposed tissues of the stomach 110 and the jejunum 112. While the plurality of arms can be independently or simultaneously actuated with respect to one another, in an exemplary embodiment, the plurality of arms on the distal ring member can be actuated prior to the actuation of the plurality of arms on the proximal ring member. As a result, the plurality of arms of the distal end of the fastener can engage the tissue of the jejunum 112, as shown in FIG. 1C. Once the fastener is engaged with the jejunum tissue 112, the applier device 126 can be moved proximally such that it is retracted within the esophagus to cause the jejunum tissue 112 to contact the stomach tissue 110, as shown in FIG. 1D. The proximal ring member can then be deployed into stomach tissue 110 that is located opposite to the already-engaged tissue of the jejunum 112, such that the plurality of arms of the fastener engage the tissue of the stomach 110, causing an anastomosis 114 to form between the stomach 110 and the jejunum 112 (FIG. 1E).

Following formation of the anastomosis 114, the applier device 126 can be extracted from the stomach 110 transorally, and any laparoscopic instruments can be removed from the surgical site. The site can then optionally be leak tested to ensure that the anastomosis is sound. Over time, the tissue walls can permanently heal together and the fastener can be passed out of the digestive tract, especially if the fastener is biofragmentable.

Figure 2:
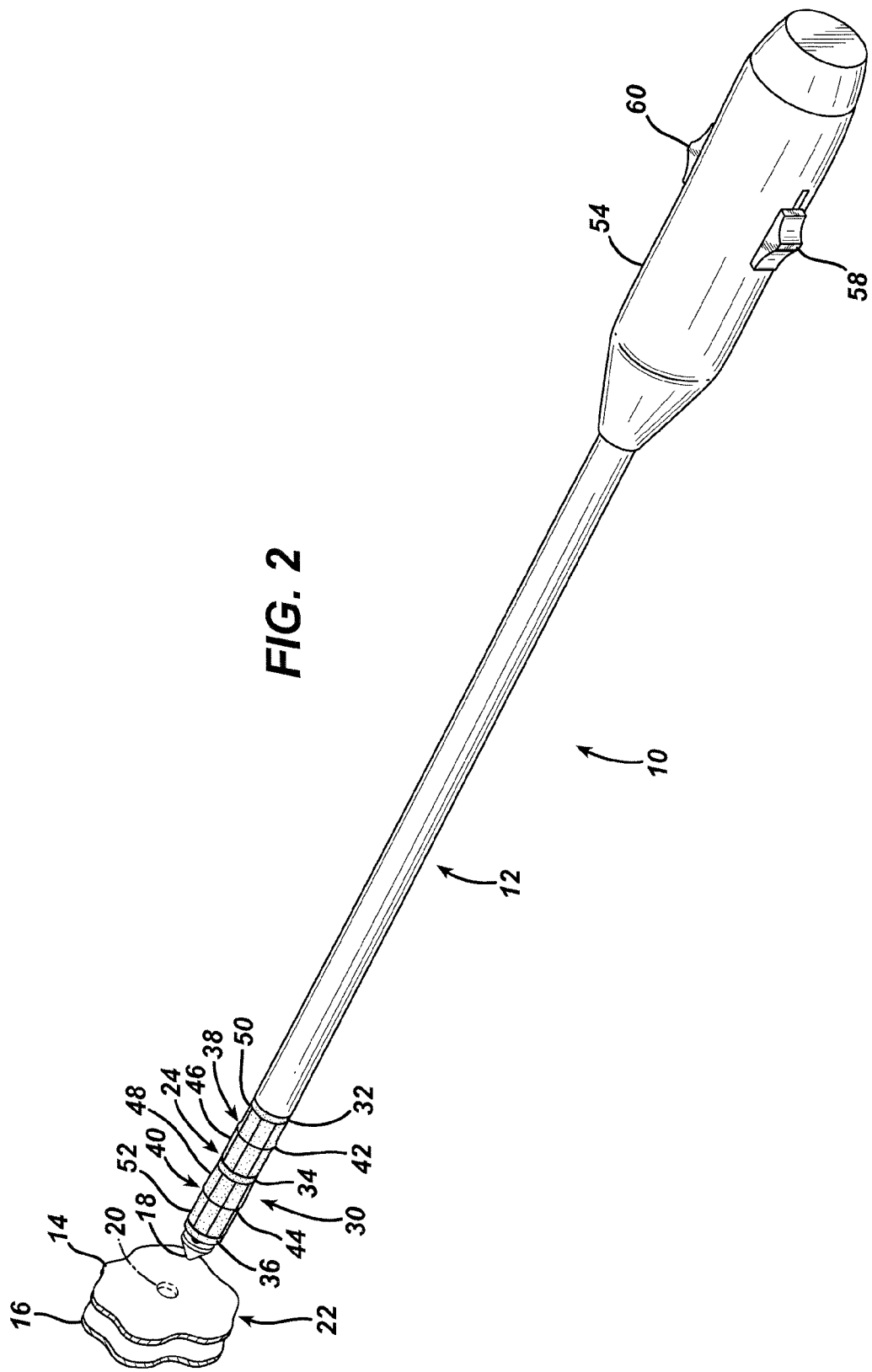
FIG. 2 is perspective view of one embodiment of an applier device having a fastener for use with the method of FIGS. 1A-1D.
Figure 3:
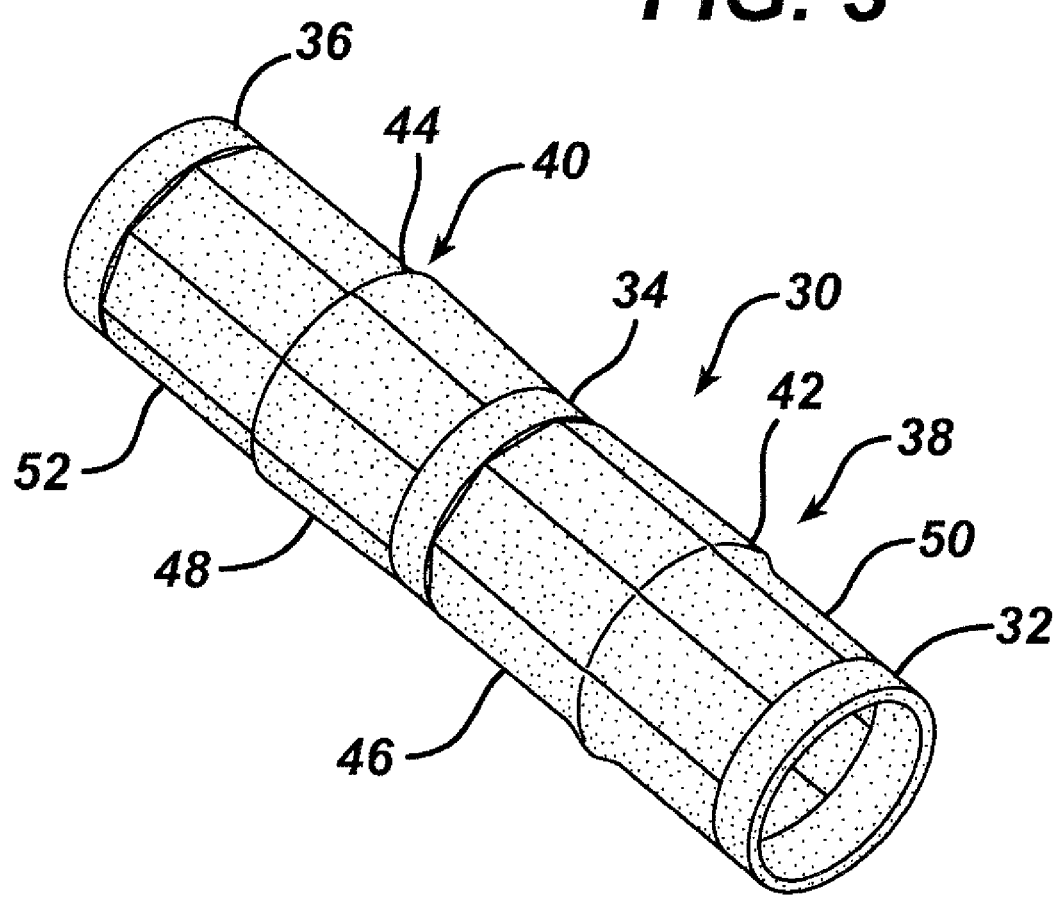
FIG. 3 is a perspective view of the fastener of FIG. 2.
Figure 4:
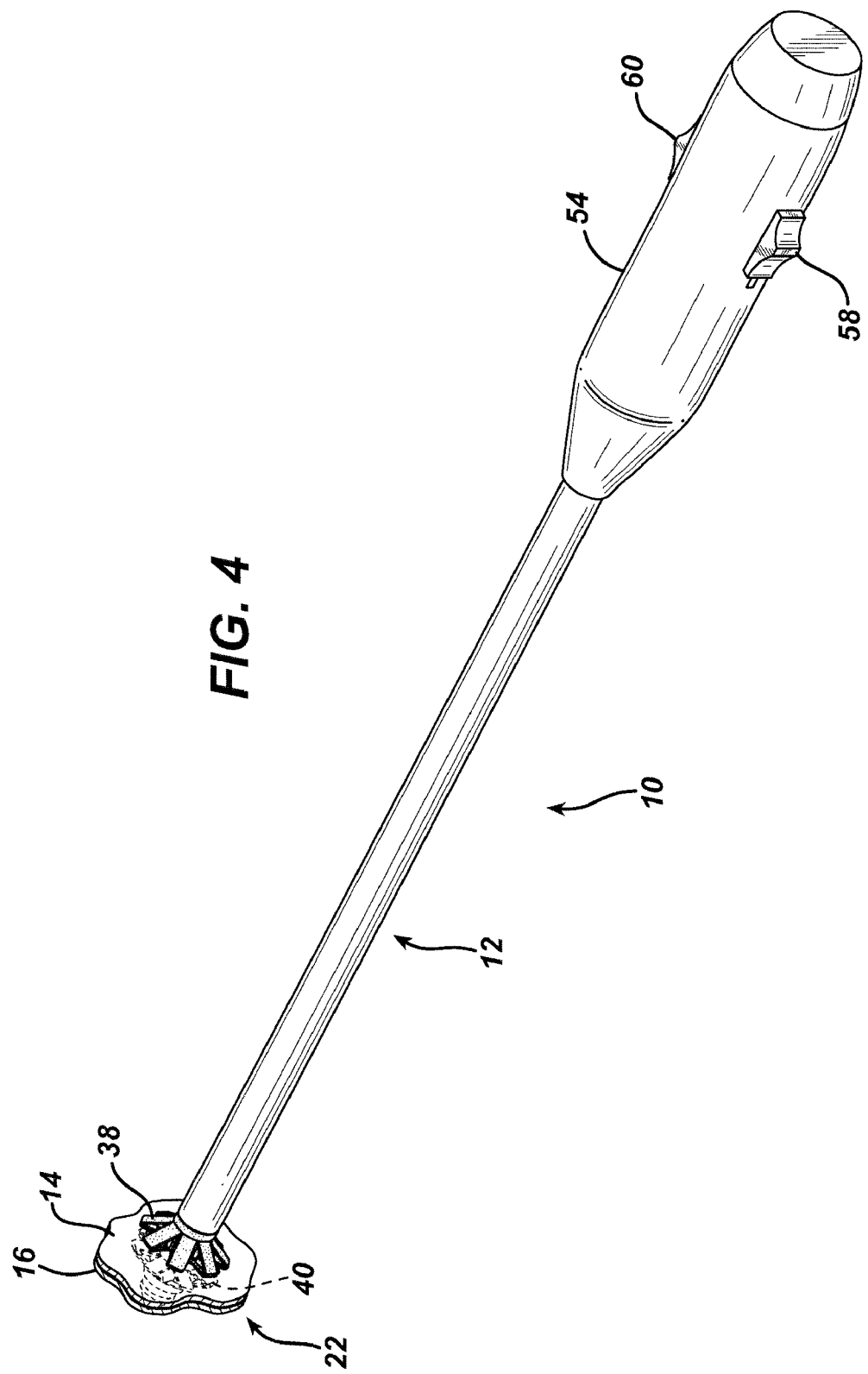
FIG. 4 is a perspective view of the applier device and fastener of FIG. 2 after actuation, where the fastener is deployed into tissue.

As noted above, a variety of types of applier devices and fasteners can be used with the method described herein form an anastomosis. While the applier device and fastener used are generally dependent upon the types of tissues being joined, one exemplary applier device and fastener is shown in FIGS. 2-6. In general, as shown in FIGS. 2 and 4, the applier device 10 includes an elongate implement portion 12 having proximal and distal ends that is dimensionally sized for insertion through a natural or created orifice. The proximal end can include a handle 54 and the distal end can include an actuation portion 24 adapted to hold a fastener 30. The distal end can also have a distal tip 18 that can be adapted to pierce through an opening 20 at an anastomosis site 22 in tissue 14, 16 to facilitate the positioning of the actuation portion 24 within the tissue 14, 16.

The elongate implement portion 12 can have virtually any configuration, and in an exemplary embodiment, the elongate implement portion 12 can be flexible such that it can be endoscopically inserted into and through an orifice. The handle 54 can be adapted to effect actuation of the fastener, and as shown the applier device 10 includes controls for effecting the actuation of the actuation portion 24 to cause deployment of the fastener 30 into tissue 14, 16. In one embodiment, the controls can include a first slide control 58 and a second slide control 60. The handle 54 can further include controls to effect illumination of the distal tip so that actuation of at least a portion of the fastener 30 in a lumen can be proximally viewed using an optics unit. The optics unit may be part of an endoscope or the applier device. While the illustrated applier device can be manually positioned and actuated, one skilled in the art will appreciate that the applier device 10 can also adapted to be remotely positioned and actuated.

Figure 5:
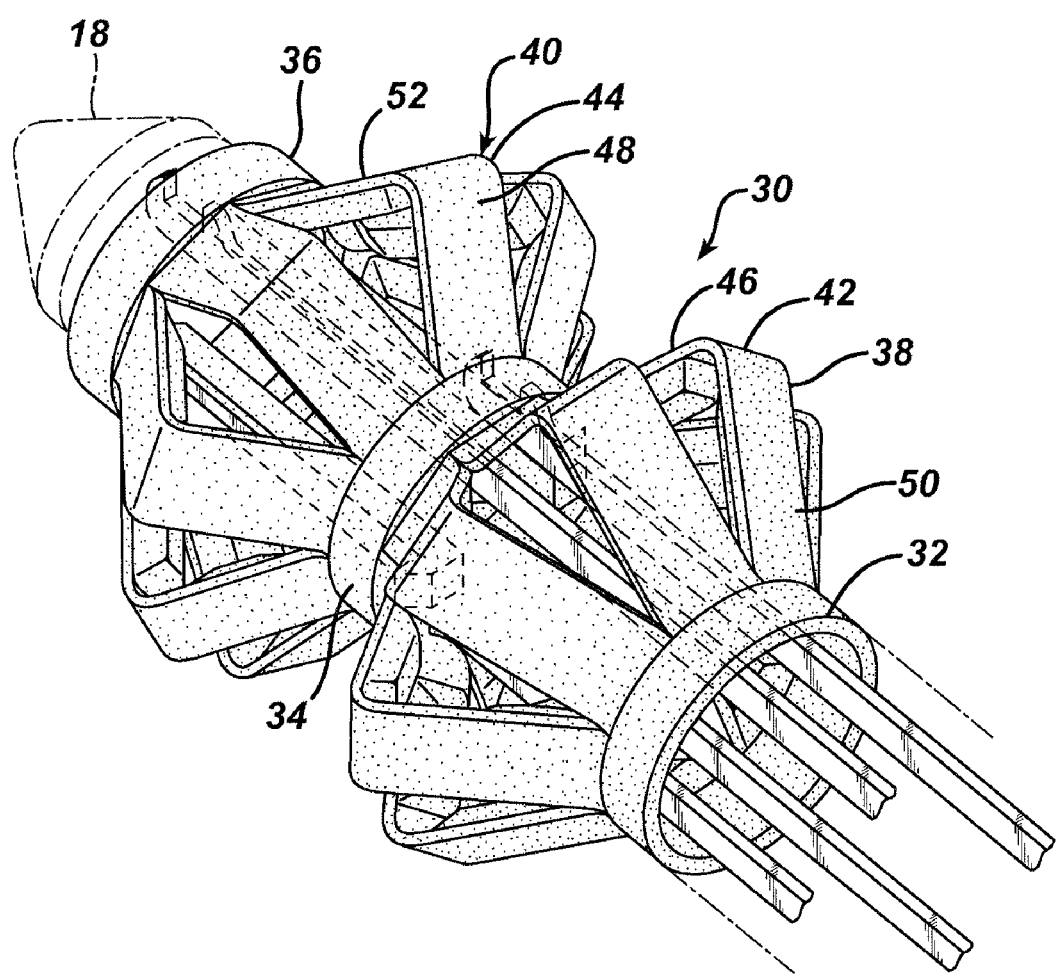
FIG. 5 is a perspective view of the fastener of FIG. 3 after deployment into tissue.
Figure 6:
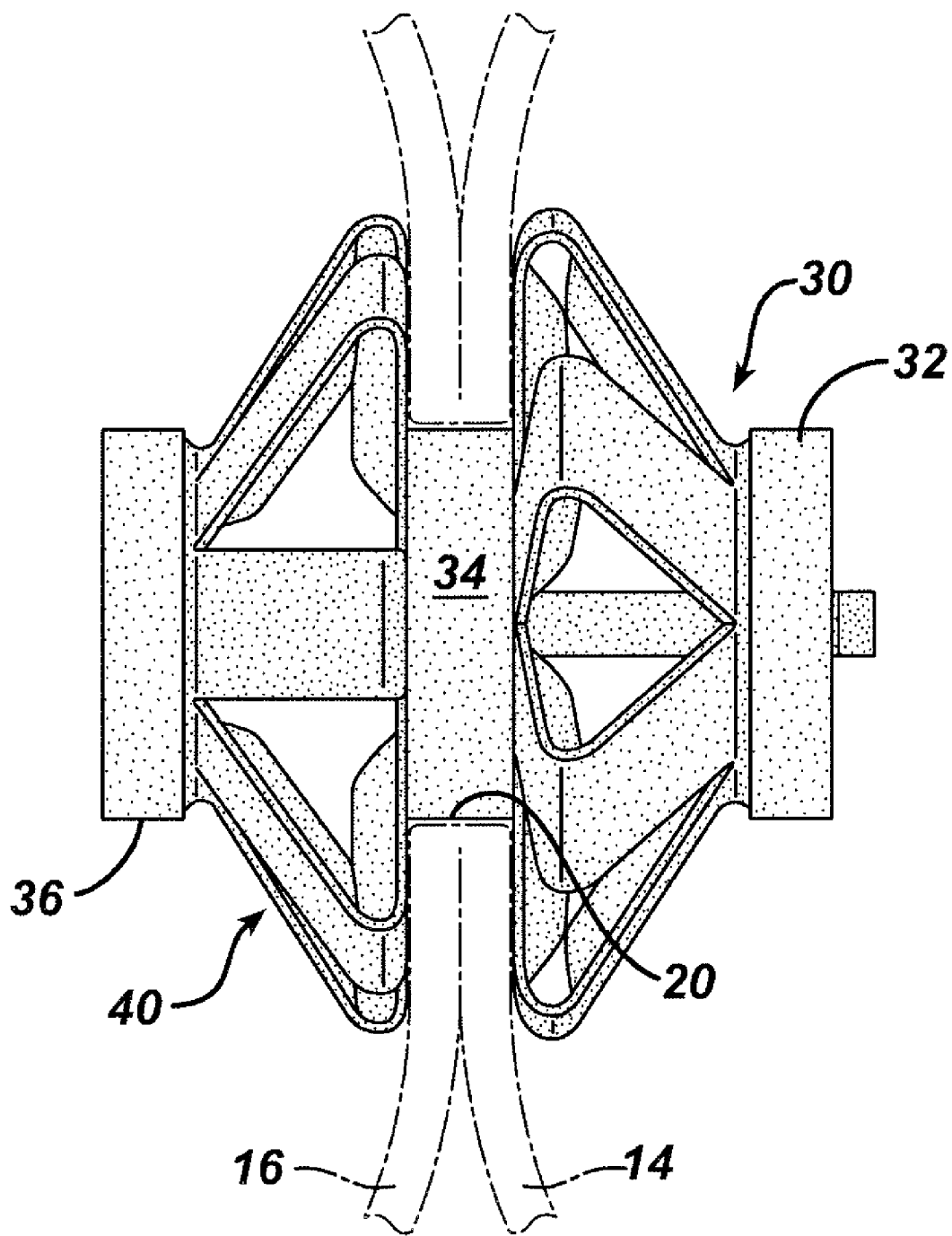
FIG. 6 is another perspective view of the fastener of FIG. 3 after deployment into tissue.

A variety of fasteners can be used with the applier device described herein, and the fasteners can generally have any configuration that is effective to engage and hold tissue. In one embodiment, as shown in FIGS. 3 and 5-6, the fastener 30 has three rings, a proximal ring 32, a center ring 34, and a distal ring 36, that are cylindrically aligned with one another. The proximal ring 32 is longitudinally attached to the center ring 34 by proximal arms 38, which in turn is longitudinally attached to the distal ring 36 by distal arms 40. Each proximal and distal arm 38, 40 is bisected respectively by a hinged joint 42, 44 that defines an inner arm segment 46, 48 that is hingedly attached to the center ring 34, and an outer arm segment 50, 52 that is also hingedly attached to the respective proximal or distal ring 32, 36. The fastener 30 can have a variety of shapes and sizes, however, in its unactuated state as shown in FIG. 3, the fastener 30 has a substantially cylindrical configuration. The relative lengths of the inner arm segments 46, 48 to the outer arm segments 50, 52 can be selected to angularly contact the tissue when the fastener 30 is deployed, and as illustrated in FIGS. 5-6, the relationship between the proximal and distal rings 32, 36 resembles a cantilevered contact with the inner arm segments 46, 48 actuating to an approximately parallel relationship to the tissue walls 14, 16. The fastener 30 can also optionally include a locking mechanism that is adapted to maintain the position of the proximal and distal arms relative to one another once the fastener is deployed into tissue. One exemplary locking mechanism (not shown) can include at least one hook that is connected to the distal ring of the fastener that can latch to the center ring or the proximal ring upon actuation thereof to maintain the distal ring in an actuated position, and/or another hook that is connected to the proximal ring that can latch to the center ring or the distal ring upon actuation thereof to maintain the proximal ring in an actuated position.

In use, and in order to effect the delivery of the fastener to tissue, the two slide controls 58, 60 on the handle 54 can be withdrawn proximally to effect actuation of the actuation portion 24, which causes the proximal and distal rings 32, 36 to move from a first resting position to a second actuated position relative to the center ring 34. As shown in FIGS. 4-6, when deployed into tissue 14, 16, the proximal and distal arms 38, 40 hinge outwardly from the longitudinal axis of the fastener 30, creating a hollow rivet or hourglass shape for apposing tissue walls 14, 16. The center ring 34 sits at a tissue junction between the lumens, and the distal and proximal rings 32, 36 can engage the opposed tissues 14, 16. The rings 32-38 can also be latched or locked to one another when actuated, as a result of the locking mechanism, to cause the fastener 30 to be held in the actuated position with bent arms 38, 40 opposing the tissue 14,16, as shown in FIG. 6. The proximal arms 38 can be staggered, as shown in FIG. 6, from distal arms 40 to create a tortuous path for the compressed tissue. Alternatively, in other embodiments, the arms 38, 40 can be aligned to directly mate to each other.

In the above embodiment, the proximal ring 36 is stationary with respect to the applier device 10, however the device 10 can also include a third control so that each of the three rings can be positioned independently from the rest, further enhancing the ability to actuate either the distal or the proximal arms 40, 38. Alternatively, the center ring 34 can be stationary with respect to the applier device 10, with controls effective to move the proximal and distal rings 32, 36 inwardly to the center ring 34. Those skilled in the art will appreciate that the applier device can further include a variety of other features known in the art and not disclosed herein, such as, by way of non-limiting example, a catch mechanism for holding the fastener to the device, and in particular to the actuation portion thereof, to prevent accidental deployment.

While FIGS. 2-6 illustrate one exemplary applier device and fastener that can be used to join a first piece of tissue to a second piece of tissue, a variety of applier devices and fasteners can be used to form an anastomosis in accordance with the method disclosed herein, such as those disclosed in commonly-owned U.S. application Ser. No. 10/675,091, filed Sep. 30, 2003, and entitled "Unfolding Anastomosis Device;" U.S. application Ser. No. 10/674,371, filed Sep. 30, 2003, and entitled "Anastomosis Wire Ring Device;" and U.S. application Ser. No. 10/675,497, filed Sep. 30, 2003, and entitled "Single Lumen Anastomosis Applier for Self-Deploying Fastener," all of which are incorporated by reference herein.

Applier devices, including portions thereof, can be designed to be disposed after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. By way of example, the applier devices that can be used herein can be reconditioned after the device has been used in a medical procedure. The device can be disassembled, and any number of the particular pieces (e.g., the fasteners, the actuation portion, and the distal tip) can be selectively replaced or removed in any combination. For example, the fasteners can be replaced by adding a new fastener cartridge to the actuation portion or by replacing the actuation portion with a fully loaded actuation portion. Upon cleaning and/or replacement of particular parts, the device can be reassembled for subsequent use either at a reconditioning facility, or by a surgical team immediately prior to a surgical procedure. Those skilled in the art will appreciate that reconditioning of an applier device can utilize a variety of techniques for disassembly, cleaning/replacement, and reassembly. Use of such techniques, and the resulting reconditioned applier device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for joining tissue, comprising:
    inserting an applier device into a stomach through a natural body orifice, the applier device having an actuation portion with a fastener disposed thereon;
    forming a first opening in a sidewall of the stomach and a second opening in a sidewall of a jejunum;
    inserting the applier device through the first and second openings such that the actuation portion and at least a portion of the fastener are between the stomach and the jejunum; and
    deploying a first portion of the fastener into the jejunum through the actuation portion of the applier device, and then moving the first portion of the fastener toward the stomach to bring the jejunum into contact with the stomach, and then deploying a second portion of the fastener into the stomach, thereby joining the stomach and jejunum to form an anastomosis between the stomach and jejunum wherein the second and first portions of the fastener respectively comprise proximal and distal ring members joined by a connecting element, the proximal and distal ring members each having a plurality of expandable arms extending therefrom that are adapted to engage tissue.

2. The method of claim 1, wherein the first and second openings are formed via a laparoscopic surgical procedure.

3. The method of claim 1, wherein the first opening is formed using a cutting member associated with a distal end of the applier device and the second opening is formed using a cutting element that accesses a site of the second opening by a laparoscopic port.

4. The method of claim 1, wherein a distal end of the applier device is used as a marker for forming the first opening.

5. The method of claim 1, further comprising expanding the first and second openings using a tapered distal end of the applier device, such that the applier device can be inserted through the first and second openings.

6. The method of claim 1, further comprising expanding the second opening using at least one grasping element such that the applier device can be inserted through the second opening.

7. The method of claim 1, wherein positioning the actuation portion includes positioning the distal ring member of the fastener such that it is adjacent to the jejunum and positioning the proximal ring member of the fastener such that it is adjacent to the stomach, such that the connecting element extends between the jejunum and the stomach.

8. The method of claim 1, wherein deploying the fastener includes disengaging the fastener from a catch located on the actuation portion that holds the fastener to the actuation portion.

9. The method of claim 1, wherein the applier device endoscopically accesses a stomach through an esophagus.

10. The method of claim 1, wherein deploying the fastener includes moving the plurality of arms of the proximal and distal ring members from a first resting position to a second actuated position such that the plurality of arms engage and hold together the jejunum and the stomach.

11. The method of claim 10, wherein the plurality of arms of the proximal and distal ring members are independently actuated to engage the jejunum and the stomach.

12. A method for forming an anastomosis, comprising:
  endoscopically inserting an applier device through a natural body orifice, through a lumen and through a first opening formed in a stomach and a second opening formed in a jejunum;
  positioning at least a portion of a fastener disposed on an actuation portion of the applier device between the stomach and jejunum; and
  deploying a first portion of the fastener into the jejunum through the actuation portion of the device, then moving the first portion of the fastener toward the stomach to bring the jejunum into contact with the stomach, and then deploying a second portion of the fastener into the stomach to form an anastomosis between the jejunum and the stomach wherein the second and first portions of the fastener respectively comprise proximal and distal ring members joined by a connecting element, the proximal and distal ring members each having a plurality of expandable arms extending therefrom that are adapted to engage tissue.

13. The method of claim 12, wherein the first and second openings are formed via a laparoscopic surgical procedure.

14. The method of claim 12, wherein the first opening is formed using a cutting member associated with a distal end of the applier device and the second opening is formed using a cutting element that accesses a site of the second opening laparoscopically.

15. The method of claim 12, further comprising expanding the first and second openings such that the applier device can be inserted therethrough.

16. The method of claim 15, wherein deploying the fastener includes moving the plurality of grasping arms of the proximal and distal ring members from a resting position to an actuating position such that the plurality of grasping arms engage the jejunum and stomach.

* * * * *